United States Patent [19]
Reusser et al.

[11] Patent Number: 4,623,644
[45] Date of Patent: Nov. 18, 1986

[54] ACYLATION OF TIRANDAMYCIC, STREPTOLIC AND SORBIC ACIDS TO CEPHALOSPORIN AND PENICILLIN NUCLEI

[75] Inventors: Fritz Reusser, Portage, Mich.; Kenneth L. Rinehart, Jr., Champaign, Ill.

[73] Assignee: The Upjohn Company, Kalamazoo, Mich.

[21] Appl. No.: 763,392

[22] Filed: Aug. 7, 1985

[51] Int. Cl.$^4$ ............... A61K 31/43; A61K 31/545; C07D 499/76; C07D 501/14
[52] U.S. Cl. .................................. 514/196; 540/228; 540/314; 540/329; 514/202; 514/209
[58] Field of Search ............... 260/239.1; 514/196, 514/202, 209; 544/28

[56] References Cited
FOREIGN PATENT DOCUMENTS
877323 7/1960 United Kingdom .

OTHER PUBLICATIONS
Reusser, F., "Tirandamycin, An Inhibitor of Bacterial Ribonucleic Acid Polymerase", *Antimicrobial Agents and Chemotherapy*, 10 (No. 4): 618–622, (1976).

*Primary Examiner*—Natalie Trousof
*Assistant Examiner*—Vera C. Clarke
*Attorney, Agent, or Firm*—Kenneth A. Weber

[57] ABSTRACT

This invention relates to the hybridization of streptolydigin, tirandamycin and sorbic acid to penicillin and cephalosporin nuclei.

7 Claims, No Drawings

ACYLATION OF TIRANDAMYCIC, STREPTOLIC AND SORBIC ACIDS TO CEPHALOSPORIN AND PENICILLIN NUCLEI

BACKGROUND OF THE INVENTION

1. Field of Invention

This invention concerns the hybridization of cephalosporins and penicillin nuclei to three organic moieties, tirandamycic and streptolic acids and sorbic acid. The ring structures of tirandamycic and streptolic acids are attached to the bactam nuclei by a methylated 6-member carbon chain which is structurally similar to sorbic acid.

Streptolic and tirandamycic acids are oxidated derivatives of streptolydigin and tirandamycin which are known antibiotics derived from cultures of *Streptomyces lydicans* and *S. tirandis*. Streptolydigin and tirandamycin are inhibitors of bacterial RNA polymerase. Cephalosporanic (7-ACA), and 6-amino penicillanic acid (6-APA) are inhibitors of bacterial cell wall synthesis.

2. Information Disclosure

Acylates of the penicillins and cephalosporins at positions C-6 and C-7, respectively are known. Chemistry and Biology of $\beta$-Lactam Antibiotics, Vol. III, R. B. Morin and M. Gorham, Ed., Academic Press, N.Y., 1982. Streptolydigin and tirandamycin have been previously described. Reusser, F., Antimicrobial Agents and Chemotherapy, 10:618-622 (1976). The hybridization of sorbic acid to penicillanic acid is known (G.B. Pat. No. 877,323) however, no reference known to inventors discloses or suggests the specific compounds herein disclosed.

SUMMARY OF INVENTION

The present invention concerns novel compounds and their use as microbial growth inhibitors. A process for making the novel compounds is also disclosed.

The present invention describes the following compounds:
(a) tirandamycylpenicillin;
(b) streptolylpenicillin;
(c) sorbylcephalosporin;
(d) tirandamycylcephalosporin; and
(e) streptolylcephalosporin.

Among the described compounds, tirandamycylpenicillin, streptolylpenicillin, tirandamycylcephalosporin and streptolylcephalosporin are preferred.

The scope of this invention includes the pharmaceutically acceptable salts of the disclosed compounds. Such salts include the following cations but are not limited to these: alkali metal ions such as potassium, sodium, lithium, alkaline earth metal ions such as magnesium or calcium and ammonium ions such as ammonium, tetralkylammonium and pyridinium.

In addition, it will be apparent to those skilled in the art that compounds of the invention herein described may contain several chiral carbons. All of the optically active, enantiomorphic and sterioisomeric forms are included within the scope of this invention. The invention also includes both the individual isomers and mixtures. Specifically, the compounds of this invention (Formula I) have chiral carbon atoms at positions C-6 of the penicillin nucleus and C-7 of the cephalosporin nucleus. The preferred forms are those with configurations identical with the configurations of the naturally occurring penicillins (e.g., penicillin G) and cephamycins (e.g., cephamycin C).

An advantage of this invention is the increased solubility of streptolydigin and tirandamycin when acylated to the nuclei of penicillin or cephalosporin.

DETAILED DESCRIPTION

The starting materials used in the disclosed compounds are either described in the literature or commercially available. The 7-ACA and 6-APA are commercially available. Sorbic acid is also commercially available. Streptolydigin and tirandamycin are natural compounds derived from the fermentation of streptomyces. A complete description of culturing, extracting and characterizing both streptolydigin and tirandamycin can be found in U.S. Pat. Nos. 3,160,560 and 3,671,728, respectively.

Streptolydigin and tirandamycin are converted to the organic acid form by the procedure of Lee, V. J. and Rinehart, K. L., J. of Antibiotic, 33:408-415 (1980), or by other conventional methods for such oxidations. The organic acids are ready for use in acylation of the desired amino group of either 6-APA or 7-ACA.

The acylation of the amino group comprises a single step and can be achieved by numerous methods known in the art. Some of these acylation methods are summarized in Cephalosporins and Penicillins, edited by Edwin H. Flynn, Academic Press (1972) at p. 83 et seq. or by 7-aminocephalosporin acylate procedures referred to in U.S. Pat. Nos. 3,671,449; 3,694,437; 3,965,098 and in British Pat. No. 1,073,530. In our process, we prefer to acylate the amino positions using the mixed anhydride procedure.

In general, the acylation uses an alkylformate such as butylformate or ethylformate which is reacted with the tertiary amine salt of streptolic or tirandamycic acid in a solvent such as acetone, acetonitrile or dimethylformamide at temperatures below 0° C., preferably between $-10°$ and 30° C. An aqueous solution of either 6-APA or 7-APA with one equivalent of base such triethylamine or sodium bicarbonate is added to the mixed anhydride. The reaction is allowed to proceed at 0° C. for 15 to 60 minutes, then warmed to room temperature for 30 to 60 minutes.

When the acylation has been completed, the hybrid compounds are obtained from the reaction mixture using conventional methods such as extraction, crystallization, column chromatography, and combinations thereof. The preferred procedure is to extract with ether.

Compounds of this invention are tested for in vitro antimicrobial activity using standard testing procedures such as the determination of minimum inhibitory concentration (MIC) by agar dilution as described in "Methods for Dilution Antimicrobial Susceptibility Tests for Bacteria that Grow Aerobically" (MFT) published January 1983 by the National Committee for Clinical Laboratory Standards, 771 East Lancaster Avenue, Villanova, PA, USA, 19084. Briefly, MIC values are determined in unsupplemented Mueller Hinton Agar (MHA). The compounds tested are diluted serially into molten MHA at 47° C. The agar is poured into petri dishes and allowed to harden. The various bacteria used for testing are grown overnight on MHA at 35° C. and transferred to Trypticase soy broth (TSB) until a turbidity of 0.5 McFarland standard is obtained. The bacteria are diluted one to twenty in TSB and inoculated on the plates (1 $\mu$l using a Steers replicator). The plates are incubated at 35° C. for 20 hours and the MIC is read to be the lowest concentration of drug that completely inhibits visible growth of the bacterium.

The compounds of this invention have broad spectrum antimicrobial activity. They are useful as surface sterilants and as additives to products where microbial populations are sought to be limited, e.g., animal feed.

The compounds of Formula I are also effective for treating bacterial infections in animals, including humans.

Various compositions of the present invention are presented for administration to humans and animals in unit dosage forms, such as tablets, capsules, pills, powders, granules, sterile parenteral solutions or suspensions, eye drops, oral solutions or suspensions, and water-in-oil emulsions containing suitable quantities of compounds of Formula I.

For oral administration, either solid or fluid unit dosage forms can be prepared. For preparing solid compositions such as tablets, the compounds of Formula I are mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with an aromatic flavoring agent. Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate. These rectal suppositories can weigh from about 1 to 2.5 grams.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

An effective quantity of the compound is employed in treatment. The dosage of the compound for treatment depends on many factors that are well known to those skilled in the art. They include for example, the route of administration and the potency of the particular compound. A dosage schedule for humans having an average weight of 70 kilograms is from about 4 to about 12 grams of compound in 2–4 doses per day, administered parenterally or in the compositions of this invention, are effective for treating bacterial infections. More specifically, the single dose is from about 2 grams to 4 grams of compound. The oral and rectal dose is from about 4 grams to about 12 grams in 2–4 doses per day. More specifically, the single dose is from about 2 grams to about 4 grams of compound.

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLES

Preparation 1

Streptolic acid

Sodium bicarbonate (0.54 g, 6.43 mmol) in water (10 mL) was added to a stirred solution of streptolydigin (3.86 g, 6.43 mmol) in t-butyl alcohol (600 mL) and deionized water (400 mL). The solution was cooled to 5° C., a solution of sodium periodate (24 g) in water (1100 mL) was added and the temperature was maintained at 5° C. for 27 h, while the reaction mixture was protected from light. Ethylene glycol (16 mL) was added and the solution was extracted with ether, dried and concentrated. The crude material was purified by partition chromatography over Celite to yield streptolic acid.

Preparation 2

Tirandamycic acid

Following the procedure outlined in Preparation 1, substituting tirandamycin for streptolydigin and making noncritical variations, tirandamycic acid may be obtained.

EXAMPLE 1

Tirandamycylpenicillin, sodium salt

Ethyl chloroformate (1.0 mL, 10.45 mmol) is added at 0° C. to a stirred solution of tirandamycic acid (4.32 g, 12.85 mmol) and triethylamine (1.75 mL, 12.55 mmol) in dry acetone (88 mL). After 5 min, the suspension is cooled to −30° C. A solution of 6-aminopenicillanic acid (6-APA, 2.66 g, 12.31 mmol) in 3% sodium bicarbonate (88 mL) is added in one portion and the temperature is maintained at 0° C. for 30 min and at room temperature for another 30 min. The clear reaction mixture is extracted with ether (2×100 mL) and the organic layer is discarded. The aqueous solution is adjusted to pH 2 by the addition of dilute hydrochloric acid and the mixture is extracted with ether (3×100 mL). The combined ether layers are extracted with 3% sodium bicarbonate (35 mL) and the aqueous solution is lyophilized to give 2.2 g (52%) of title compound.

Anal. calc'd for $C_{26}H_{33}N_2Na_2O_8S$: mol wt, 579.1753 (M+Na). Found: mol wt, 579.1745 (HRFABMS).

EXAMPLE 2

Streptolylpenicillin, sodium salt

Following the general procedures outlined in Example 1, 6-APA may be acylated with streptolic acid to yield the title compound. Reactants are used in the following proportions: streptolic acid (0.206 g, 0.644 mmol), triethylamine (0.088 mL, 0.628 mmol), ethyl chloroformate (0.05 mL, 0.523 mmol), 6-APA (0.133 g, 0.616 mmol), 3% sodium bicarbonate (4.4 mL) and acetone (5 mL).

Anal. calc'd for $C_{26}H_{30}N_2Na_2O_7S$: mol wt, 563.1804. Found: mol wt, 563.1774 (HRFABMS).

EXAMPLE 3

7-Sorbylcephalosporin, sodium salt

Following the general procedures outlined in Example 1, 7-ACA may be acylated with sorbic acid to yield the title compound. Reactants are used in the following proportions: sorbic acid (0.36 g, 3.21 mmol), triethylamine (0.44 mL, 3.16 mmol), ethyl chloroformate (0.25 mL, 2.61 mmol), 7-ACA, (0.84 g, 3.08 mmol), 3% sodium bicarbonate (22 mL) and acetone (22 mL).

Anal. calc'd for $C_{16}H_{17}N_2Na_2O_6S$: mol wt, 411.0603 (M+Na). Found: mol wt, 411.0607 (HRFABMS).

EXAMPLE 4

Tirandamycylcephalosporin, sodium salt

Following the general procedures outlined in Example 1, 7-ACA may be acylated with tirandamycic acid to yield the title compound. Reactants are used in the following proportions: tirandamycic acid (1.08 g, 3.21 mmol), triethylamine (0.44 mL, 3.16 mmol), ethyl chloroformate (0.25 mL, 2.61 mmol), 7-ACA (0.84 g, 3.08 mmol), 3% sodium bicarbonate (22 mL) and acetone (22 mL).

Anal. calc'd for $C_{28}H_{33}N_2NaO_{10}S$: mol wt, 612. Found: mol wt, 613 (M+H, FABMS).

EXAMPLE 5

Streptolylcephalosporin, sodium salt

Following the general procedures outlined in Example 1, 7-ACA may be acylated with streptolic acid to yield the title compound. Reactants are used in the following proportions: streptolic acid (0.206 g, 0.644 mmol), triethylamine (0.088 mL, 0.63 mmol), ethyl chloroformate (0.050 mL, 0.522 mmol), 7-ACA (0.175 g, 0.643 mmol), sodium bicarbonate (3%, 4.4 mL) and acetone (5 mL).

Anal. calc'd for $C_{28}H_{33}N_2Na_2O_9S$: mol wt, 619.1702 (M+Na). Found: mol wt, 619.1689 (HRFABMS).

FORMULAE

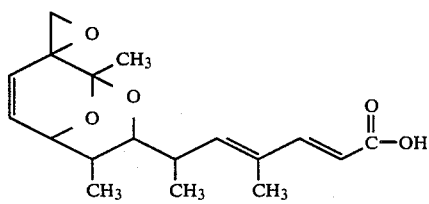

Streptolic Acid

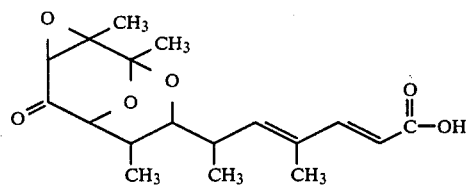

Tirandamycic Acid

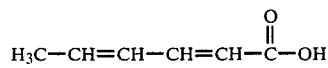

Sorbic Acid

We claim:
1. A compound selected from the group consisting of:
   (a) tirandamycylpenicillin;
   (b) streptolylpenicillin;
   (c) sorbylcephalosporin;
   (d) tirandamycylcephalosporin;
   (e) streptolylcephalosporin;
   and a pharmaceutically acceptable salt thereof.
2. A compound according to claim 1 wherein the compound is tirandamycylpenicillin or a pharmaceutically acceptable salt thereof.
3. A compound according to claim 1 wherein the compound is streptolylpenicillin or a pharmaceutically acceptable salt thereof.
4. A compound according to claim 1 wherein the compound is sorbylcephalosporin or a pharmaceutically acceptable salt thereof.
5. A compound according to claim 1 wherein the compound is tirandamycylcephalosporin or a pharmaceutically acceptable salt thereof.
6. A compound according to claim 1 wherein the compound is streptolylcephalosporin or a pharmaceutically acceptable salt thereof.
7. A method of treating bacterial infections in animals in need thereof which comprises administering to said animals an effective amount of a compound selected from the group consisting of:
(a) tirandamycylpenicillin;
(b) streptolylpenicillin;
(c) sorbylcephalosporin;
(d) tirandamycylcephalosporin;
(e) streptolylcephalosporin;
and a pharmaceutically acceptable salt thereof.

* * * * *